United States Patent
Berney

(10) Patent No.: US 8,674,320 B2
(45) Date of Patent: Mar. 18, 2014

(54) DECONVOLUTION OF TIME-GATED CATHODOLUMINESCENCE IMAGES

(71) Applicant: Attolight SA, Lausanne (CH)

(72) Inventor: Jean Berney, Lausanne (CH)

(73) Assignee: Attolight SA, Lausanne (CH)

( * ) Notice: Subject to any disclaimer, the term of this patent is extended or adjusted under 35 U.S.C. 154(b) by 0 days.

(21) Appl. No.: 13/795,291

(22) Filed: Mar. 12, 2013

(65) Prior Publication Data

US 2013/0193342 A1    Aug. 1, 2013

Related U.S. Application Data

(63) Continuation of application No. PCT/EP2011/066105, filed on Sep. 16, 2011.

(30) Foreign Application Priority Data

Oct. 1, 2010    (EP) .................................. 10186301

(51) Int. Cl.
*H01J 29/58* (2006.01)
*H01J 49/08* (2006.01)
*G21K 1/00* (2006.01)

(52) U.S. Cl.
USPC ........ 250/399; 250/306; 250/307; 250/396 R; 250/492.3

(58) Field of Classification Search
USPC ................... 250/399, 306, 307, 396 R, 492.3
See application file for complete search history.

(56) References Cited

U.S. PATENT DOCUMENTS

| | | | |
|---|---|---|---|
| 4,117,323 A | 9/1978 | Greer et al. | |
| 4,929,041 A | 5/1990 | Vahala et al. | |
| 5,034,903 A | 7/1991 | Alfano et al. | |
| 5,393,976 A | 2/1995 | Koike | |
| 5,569,920 A | 10/1996 | Phang et al. | |
| 6,122,042 A | 9/2000 | Wunderman et al. | |
| 7,557,359 B2 * | 7/2009 | Ward et al. | 250/423 F |
| 8,440,969 B2 * | 5/2013 | Moore et al. | 250/307 |
| 2004/0046120 A1 | 3/2004 | Moses et al. | |
| 2004/0112964 A1 | 6/2004 | Empedocles et al. | |
| 2005/0242364 A1 | 11/2005 | Moustakas et al. | |
| 2007/0086915 A1 | 4/2007 | LeBoeuf et al. | |
| 2010/0059672 A1 | 3/2010 | Zeile | |

FOREIGN PATENT DOCUMENTS

DE        203 07 617        8/2003

(Continued)

OTHER PUBLICATIONS

Mei et al., "Determination of nitrogen-related defects in N-implanted ZnO films by dynamic cathodoluminescence", Nucl. Instr. and Meth, in Phys. Res., 2005, 307-311.

(Continued)

*Primary Examiner* — Nikita Wells
(74) *Attorney, Agent, or Firm* — Pearne & Gordon LLP

(57) ABSTRACT

A method for generating a cathodoluminescence map comprising the steps of: generating an intensity modulated charged particle beam; focusing said charged particle beam on a specimen; gating temporally the cathodoluminescence emitted by said specimen to provide time-gated cathodoluminescence; measuring the time-gated cathodoluminescence for different charged particle beam positions on the specimen to generate a cathodoluminescence map; deconvoluting the cathodoluminescence map to improve the resolution of said cathodoluminescence map. The invention further provides devices for carrying out such methods.

14 Claims, 2 Drawing Sheets

(56) References Cited

FOREIGN PATENT DOCUMENTS

| EP | 2 085 758 A2 | 1/2009 |
|---|---|---|
| JP | 60247140 A | 12/1985 |
| JP | 61195336 A | 8/1986 |
| JP | 62027630 A | 2/1987 |
| JP | 63061938 A | 3/1988 |
| JP | 2008249478 A | 10/2008 |
| WO | 95/10768 A1 | 4/1995 |
| WO | 2006093966 A2 | 9/2006 |
| WO | 2012041721 A1 | 4/2012 |

OTHER PUBLICATIONS

Jeol, "Spectral Cathodoluminescence Mapping of Quartz Grains", web article, http://www.jeol.com.au/news2.html.

Herman, et al., "Heterointerfaces in quantum wells and epitaxial growth processes; Evaluation by luminescence techniques", Journal of Applied Physics, 1991, R1-R52.

Wada, et al., "A High Resolution Cathodoluminescence Microscopy Utilizing Magnetic Field", Japanese Journal of Applied Physics/Part 2, 1988, L1952-L1954.

Merano, et al., "Probing carrier dynamics in nanostructures by picosecond cathodoluminescence", Nature Publishing Group, 2005, 479-482.

Pezzotti, et al., "Looking at the nanomechanics of electronic devices under the scanning electron microscope", web article, http://spie.org/x25301.xml?ArticleID=x25301.

International Search Report dated Nov. 25, 2011 for PCT/EP2011/066105.

Chan, et al., "Microtomography and improved resolution in cathodoluminescence microscopy using confocal mirror optics", Review of Scientific Instruments, Oct. 2004, vol. 75, No. 10.

\* cited by examiner

DECONVOLUTION OF TIME-GATED CATHODOLUMINESCENCE IMAGES

FIELD OF THE INVENTION

The present invention relates to methods and devices for generating cathodoluminescence maps. In particular, but not exclusively, the present invention relates to non-destructive methods and devices to measure cathodoluminescence maps which have improved spatial resolution and/or provide depth resolution e.g. 3D cathodoluminescence maps.

BACKGROUND TO THE INVENTION

Cathodoluminescence is an excitation spectroscopy technique that consists in irradiating a luminescent specimen with an electron beam and measuring the induced emitted light. Within the interaction or generation volume of the incident electron beam with the specimen, the incident electrons undergo a series of elastic and inelastic scattering events, resulting in the generation of excited charge carriers i.e. electron-hole pairs. These electron-hole pairs diffuse and eventually recombine emitting photons; these photons form a cathodoluminescence signal.

The photons emitted by the recombining electron-hole pairs are detected using a photo-detector. By scanning the electron beam over the surface of the specimen and recording the cathodoluminescence signal intensity as a function of the electron beam position on the specimen, a spatially resolved cathodoluminescence map can be formed.

As the number of electron-hole pairs produced, and in turn the number of electron-hole pair recombination's which occur to emit photons, is dependent on the properties of the luminescent specimen, the cathodoluminescence map will thus be indicative of the properties of the luminescent specimen.

The cathodoluminescence signal can also be resolved spectrally. In a spectrally resolved cathodoluminescence experiment, a light-dispersing element disperses the cathodoluminescence signal and a single channel or a multi-channel photo-detector measures one specific spectral interval or multiple spectral intervals respectively. By scanning the electron beam over the surface of the specimen and recording the cathodoluminescence signal intensity over one on more spectral intervals as a function of the electron beam position on the specimen, a spatially and spectrally resolved cathodoluminescence map can be produced. Spectral information gives additional information about the luminescent properties of a specimen.

Cathodoluminescence is advantageous over purely optical excitation spectroscopy methods, such as photoluminescence, because it can feature higher spatial resolution; the highly focused electron beam of a scanning electron microscope can be used to excite a very small area of the specimen and thus information on the optical properties of a local area of the luminescent specimen can be obtained.

Yet, even with a nanometer size probe, the overall spatial resolution of a cathodoluminescence map is limited by the generation volume of the incident electron probe (the generation volume is the volume of the luminescent specimen which is excited by the incident electrons), and charge carrier diffusion within the specimen.

Indeed, depending on the material investigated, electron-hole pair recombination can occur microns away from the excitation spot, thus severely compromising the resolution of the cathodoluminescence map.

While it is extremely complicated to calculate charge carrier diffusion, the profile of the generation volume can be both accurately computed and measured. A Monte Carlo technique can simulate the electron trajectory within a specimen using probability distributions for scatterings events and charge carrier density thereof inferred. Luminescence theory can then relate the charge carrier density to the luminescence spectral intensity. FIG. 1 shows the result of two Monte Carlo simulations in bulk Gallium Nitride for (a) 1 keV and (b) 5 keV electron beam probe energy. It is known to embed quantum wells in a specimen to experimentally measure the generation volume.

A possible solution to improve the spatial resolution of cathodoluminescence maps is to work with low incident electron beam probe energy, e.g. a few keV or below. This reduces the generation volume of incident electrons. However, disadvantageously, at low acceleration voltages, only shallow sub-surface features of the specimen can be accessed.

A solution to limit the impact of charge carrier diffusion on spatial resolution has been proposed. By operating the microscope in stroboscopic mode, and temporally gating the CL signal detection so that it only records the onset of the charge carrier diffusion process, they suggested that the spatial resolution could be improved. They used a beam blanker to pulse the electron beam. Unfortunately, such a technology cannot guarantee the stability of the beam while switched on and off; the space resolution starts to degrade for pulses having short temporal width (<1 ns). Since typical carrier mobility in semiconductors is of the order of nanometers per picosecond, the advantage of their technique is limited to materials having a large diffusion length (>1 μm).

D. S. H. Chan et al. disclose that confocal mirror optics might be used to collect the cathodoluminescence light (Review of Scientific Instruments 75 (2004), p. 3191). With such a solution, the resolution limit is no longer determined by the beam and specimen properties but by the light optics technology. Three-dimensional visualisation of the specimen is possible. Yet, the expected lateral resolution is of the order of a few hundred of nanometers and in-depth resolutions of the order of one micrometer at best. Thus, the solution does not provide satisfactory lateral and depth resolution.

Patent US2010059672 discloses how a 3D cathodoluminescence data set can be generated. US2010059672 discloses the use of an electron probe to excite the surface of a specimen and different measurement channels (e.g. EBSD, cathodoluminescence, secondary electrons etc.) to characterize it. An ion beam removes (by abrasion) the measured layer of the specimen. These operations are repeated as many times as required and a 3D cathodoluminescence can be reconstructed layer by layer. Disadvantageously, with such a method, the volume that is measured is destroyed; ions used for abrasion may penetrate the specimen and alter its optical properties; space resolution is limited by the size of the generation volume and by charge carrier diffusion.

US2004046120 discloses markers (nanoparticles) are injected in a cell so that they stick to different features of the cell. The markers are then observed with a cathodoluminescence microscope. A bright spot is indicative of the presence of a marker. A fuzzy appearance of the bright spots indicates that the markets are close to a membrane. This document teaches to deduce how far a marker is from a membrane using deconvolution.

Disadvantageously, the invention of US2004046120 does not yield spectroscopic information. The cathodoluminescence method is used to reveal the position of markers only, but does not give any information on the spectroscopic properties of the investigated specimen. US2004046120 therefore discloses generating 3D images whose contrasts depend on the structure of the specimen, but does not disclose how to generate 3D images whose contrasts depend on the spectral properties of the specimen. Furthermore, US2004046120 discloses measuring the cathodoluminescence of nanoparticles i.e. cathodoluminescence of nanoparticles showing up on cathodoluminescence spectra, but does not discloses measuring the cathodoluminescence of the specimen.

Pezzotti G. et al. in Micro/Nano Lithography look at the nanomechanical properties of electronic devices under the scanning electron microscope. This document discloses the extraction of stress information from a cathodoluminescence spectrum by applying known mathematical transformations. The convoluted extracted stress data is deconvoluted and a stress information is generated which is free from the blurring effect of the generation volume. The document is limited to disclosing how to deconvolute a stress map which shows mechanical information, to enhance its spatial resolution. The document fails to disclose how to deconvolute a spectrally resolved cathodoluminescence map (i.e. a set of cathodoluminescence data associated with different excitation positions) to enhance its spatial resolution. Furthermore, the document fails to disclose how to spatially deconvolve a spectrum. Additionally, the method disclosed is limited for use on a specimen with a very short diffusion length, as it is not disclosed how to reduce electron-hole diffusion artifacts.

It is an aim of the present invention to obviate or mitigate one or more of the aforementioned disadvantages.

The publication "*Heterointerfaces in quantum wells and epitaxial growth processes; Evaluation by luminescence techniques*" discloses how optical and structure properties of quantum-well heterostructures can be correlated in detail, and how these properties may be connected with the parameters of an epitaxial growth process. It is disclosed how luminescence techniques, mainly photoluminescence and cathodoluminescence imaging, may be used for evaluation of the structural disorder on the atomic scale, which occurs at the growth surfaces creating the interfaces of the quantum-well heterostructures.

The publication "*A High Resolution Cathodoluminescence Microscopy Utilizing Magnetic Field*" discloses a principle to improve spatial resolution of cathodoluminescence microscopy. The principle is to block the lateral diffusion by placing carriers in a circular orbit in terms of the Lorentz force under a vertical magnetic field.

The publication "*Probing carrier dynamics in nanostructures by picoseconds cathodoluminescence*" discloses the application of a time resolved cathodoluminescence set-up to describe carrier dynamics with a single gallium-arsenide-based pyramidal nanostructures with a time resolution of 10 picoseconds and a spatial resolution of 50 nanometres. The behaviour of the charge carriers are monitored.

SUMMARY OF THE INVENTION

According to a first aspect of the present invention there is provided a method for generating a cathodoluminescence map comprising the steps of:
  generating an intensity modulated charged particle beam;
  focusing said charged particle beam on a specimen;
  gating temporally the cathodoluminescence emitted by said specimen to provide time-gated cathodoluminescence;
  measuring the time-gated cathodoluminescence for different charge particle beam positions on the specimen to generate a cathodoluminescence map;
  deconvoluting the cathodoluminescence map to improve the resolution of said cathodoluminescence map.

Preferably, the cathodoluminescence map is generated using cathodoluminescence emitted by the specimen. The step of measuring the time-gated cathodoluminescence comprises measuring the time-gated cathodoluminescence emitted by the specimen.

A cathodoluminescence map may comprise a plurality of cathodoluminescence measurements. A cathodoluminescence map which comprises a plurality of cathodoluminescence measurements may be used to deconvolve a single cathodoluminescence measurement.

Because the method of the present invention measures time-gated cathodoluminescence which may or may not be spectrally resolved for different charged particle beam positions on the specimen, and uses the measured time-gated cathodoluminescence to generate a cathodoluminescence map, the method can be used to improve the resolution of said cathodoluminescence map regardless of whether or not the cathodoluminescence is spectrally resolved.

The use of a charged particle beam, such as an electron beam, limits the abrasion of the specimen surface. Preferably, the charged particle beam is configured such that the charged particles within the beam have a momentum which is too small to significantly abrade the surface of the specimen.

For the scope of this invention, cathodoluminescence is generalized to an excitation spectroscopy that comprises irradiating a luminescent specimen with a charged particle beam and measuring the induced emitted light. The charge particle beam may be an electron beam. It will be understood that method of the present invention is not limited to use with an electron beam; any other suitable charged particle beam could be used instead.

The step of deconvoluting the cathodoluminescence map to improve the resolution of said cathodoluminescence map, may comprise deconvoluting the cathodoluminescence map to improve the spatial resolution to said cathodoluminescence map. The step of deconvoluting the cathodoluminescence map to improve the resolution of said cathodoluminescence map, may comprise deconvoluting the cathodoluminescence map to improve the lateral spatial resolution to said cathodoluminescence map. The step of deconvoluting the cathodoluminescence map to improve the resolution of said cathodoluminescence map, may comprise deconvoluting the cathodoluminescence map to improve the depth resolution to said cathodoluminescence map.

The modulated charged particle beam may be a modulated electron beam or a modulated ion beam.

The method may further comprise the step of modulating the charged particle beam and choosing a time-gate such that, electron-hole diffusion, along a particular direction within the specimen, during a time-gate interval, is of the same order of magnitude, or smaller than, the improved spatial resolution of said cathodoluminescence map along said direction.

Preferably, the time gate which is used to temporally gate the cathodoluminescence emitted by said specimen has a width smaller than 1 ns.

The time-gated cathodoluminescence may be measured directly so that the cathodoluminescence signal out of the time-gate temporal boundaries is not recorded.

Time-resolved cathodoluminescence may first be measured and then the time-resolved cathodoluminescence may be integrated over a time-gate to produce time-gated cathodoluminescence. Thus, the time-resolved cathodoluminescence is recorded.

The method may comprise the step of applying an offset to a time gate which is used to temporally gate the cathodoluminescence emitted by said specimen. Preferably, the offset of the time-gate may be modified. Thus, the time gate can be adjusted so that it measures the onset of the time-resolved cathodoluminescence signal.

The method may further comprise the step of, discretizing all or part of a volume of the specimen into a region of elementary volumes. These elementary volumes may also be referred to as mesh volumes or mesh elements.

The method may further comprise the step of determining the contribution of each elementary volume within the specimen to the measured cathodoluminescence. Thus, the measured cathodoluminescence which is used to form the cathodoluminescence map can be proportioned between the different elementary volumes within the specimen and the measured cathodoluminescence is equal to the sum of all elementary volume contributions.

Preferably, the method comprises the step of choosing elementary volumes either of whose volume, lateral extension or height is smaller than a generation volume. The generation volume is the volume of the specimen which is excited by the incident charged particle beam. The deconvolution step may then effectively increase the lateral resolution of the cathodoluminescence map and/or provide depth resolution to said cathodoluminescence map.

The method may further comprise the step of determining a generation volume, wherein the generation volume is the volume of a specimen which is excited by a modulated charged particle beam when the modulated charged particle beam is focused at a point on a surface of the specimen. Therefore, it is the generation volume of the specimen which contributes to a measured time-gated cathodoluminescence when the charged particle beam is focused at any one point on a specimen.

The method may further comprise the step of determining the contribution of the different elementary volumes to the measured cathodoluminescence when they overlap with a generation volume.

The method may further comprise the step of defining a set of parameters which describe an excitation state of the elementary volumes. This excitation state may be similar to the one generated by the modulated electron beam when the time-gated cathodoluminescence is measured. The excitation state may be different to the excitation state generated by the modulated electron beam when the time-gated cathodoluminescence is measured. For example, the set of parameters might specify that the electron-hole pair density is uniform and thermalized (i.e. the electron-hole pair energy distribution is ruled by the Fermi-Dirac statistic for a given temperature) over all elementary volumes. The deconvolution step may comprise determining the cathodoluminescence emitted by each elementary volume for the given set of parameters characterizing each elementary volume. The cathodoluminescence emitted by an elementary volume for a given set of parameters may be referred to as the elementary cathodoluminescence (or processed or deconvoluted cathodoluminescence).

The method may further comprise the step of determining a relationship between the elementary cathodoluminescence emitted by an elementary volume and the contribution of the same elementary volume to the measured cathodoluminescence when it overlaps with a generation volume. The elementary cathodoluminescence emitted by an elementary volume is the cathodoluminescence emitted by an elementary volume for a pre-defined set of parameters. Thus, the measured cathodoluminescence is equal to the sum of all elementary volume contributions in terms of elementary cathodoluminescence.

Preferably, the intensity modulated beam current is small enough, so that the contribution of the cathodoluminescence emitted by an elementary volume is proportional to the electron-hole pair density within the elementary volume. Thus many-body interactions (i.e. interactions between electrons, holes or any other quasi-particles) do not significantly alter the luminescence properties of the electron-hole pair gas and in turn the cathodoluminescence emission.

For any particular type of specimen and using well know methods, it is possible to determine within a specimen the generation volume and the contribution to the measured cathodoluminescence made by different elementary volumes which overlap with said generation volume. For example, if the specimen is of a known type, based on the know properties of that specimen it is possible to determine the generation volume and the contribution of different elementary volumes within specimen to cathodoluminescence generated by that specimen when excited by a charged particle beam having a given energy. Alternatively, by carrying out known tests on a test sample which is similar to the specimen, it is possible to determine the generation volume and the contribution of different regions within a generation volume to cathodoluminescence generated by that specimen when excited by a charged particle beam having a given energy.

Knowing how the elementary cathodoluminescence of each elementary volumes is related to the measured cathodoluminescence, i.e. knowing that measured cathodoluminescence is equal to the sum of all elementary volume contributions and knowing how each elementary volume contribution can be written in terms of elementary cathodoluminescence (and knowing it for each point on the cathodoluminescence map corresponding to each of the positions on the surface of the specimen at which the intensity modulated charged particle beam was focused), it is possible to deconvolute the time-gated cathodoluminescence map. This is done by solving a multiple equation system, wherein each equation states that measured cathodoluminescence is equal to the sum of all elementary volume contributions. The value for the elementary cathodoluminescence of each elementary volume is obtained.

When this is done for the elementary cathodoluminescence coming from all elementary volumes, a deconvoluted cathodoluminescence map can be constructed. This map shows the cathodoluminescence emitted by each elementary volume for said given set of parameters. If the elementary volumes are smaller than the generation volumes which overlap with them, the deconvolution step may then effectively increase the lateral resolution of the cathodoluminescence map and provide depth to the cathodoluminescence map.

Preferably, the region of elementary volumes includes each of the generation volumes generated during the time-gated cathodoluminescence mapping. Thus, all the cathodoluminescence contributions are taken into account in the deconvolution and the accuracy of the said deconvolution is improved.

The step of discretizing all or part of a volume of the specimen into a region of elementary volumes may comprise discretizing all or part of a volume of the specimen into a single layer of elementary volumes. Thus, the deconvolution step yields a 2D deconvoluted cathodoluminescence map showing the cathodoluminescence emitted by each elementary volume within the layer for said set of parameters. When the elementary volumes are laterally smaller than the generation volume, said 2D deconvoluted cathodoluminescence map features improved lateral spatial resolution because the deconvolution removes the contribution made to the measured cathodoluminescence by the elementary volumes within a generation volume which are lateral to the position on the surface of the specimen at which the intensity modulated charged particle beam was focused.

The elementary volumes may comprise one or more elementary volumes located below the surface of the specimen. The deconvolution step then yields a map showing the cathodoluminescence emitted by each elementary volume, one or more of which being buried below the surface. Thus, the deconvoluted cathodoluminescence map shows in-depth cathodoluminescence information and forms a 3D cathodoluminescence map.

It is also possible to choose elementary volumes located at various depths below the surface of the specimen so that a 3D cathodoluminescence maps representing varying depths of the specimen can be obtained.

Preferably, the method comprises the step of discretizing all or part of a volume of the specimen into two or more layers of elementary volumes. Thus the step of deconvoluting the measured time-gated cathodoluminescence provides a 3D cathodoluminescence map, consisting in two or more 2D cathodoluminescence maps each of which represent cathodoluminescence emitted from planes which are at different depths of the specimen. It is possible to provide elementary volumes within one or more of said layers with lateral extension that are smaller than the lateral expansion of the generation volumes that overlap with each of them so that the deconvolution step also improves lateral resolution.

For example, it is possible to discretize part or all the specimen volume in; regions within the specimen which lie between a surface of the specimen and 1 nm depth; regions within the specimen which lay between 1 nm-2 nm depth; regions within the specimen which lay between 2 nm-3 nm depth etc. In doing this, the cathodoluminescence emitted from elementary volumes at planes which lie at different depths within the specimen, can be determined. Thus, the measured cathodoluminescence can be proportioned to form a plurality of 2D cathodoluminescence maps each of which are formed by cathodoluminescence emitted at planes which lie at different depths of the specimen; therefore each of which represent planes which lie at different depths of the specimen. For example a 2D cathodoluminescence map which is formed using only cathodoluminescence emitted by a plane within the specimen which lies between surface and 1 nm can be provided; a 2D cathodoluminescence map formed using only cathodoluminescence emitted from a plane within the specimen which lies between 1 nm and 2 nm can be provided; and a 2D cathodoluminescence map formed using only cathodoluminescence emitted from a plane within the specimen which lies between 2 nm and 3 nm can be provided; etc.

The modulated charged particle beams used in the above method preferably comprises energy which is less than the energy required to abrade or damage the specimen. The method may comprise the step of configuring the modulated charged particle beam so that it comprises energy which is less than the energy required to abrade or damage the specimen. Thus, the method is a non-destructive method ensuring that when the modulated charged particle beam impacts the specimen it will not damage or abrade the specimen.

Deconvolution may comprise the step of solving a system of linear or non-linear equations.

Preferably, deconvolution may comprise the steps of solving a system of linear or non-linear equations with a least square method.

Preferably, the number of excitation points on the measured time-gated cathodoluminescence map is more than or equal to the number of elementary volumes. The more excitation points the better the accuracy of the deconvolution step because it reduces the impact of measurement noise.

In case the modulated charge carrier beam is a modulated electron beam, the intensity modulated electron beam may be generated from a photocathode illuminated by a beam of light.

A beam spot of the modulated charged particle beam may be smaller than 1 µm. The beam spot may have a diameter which is smaller than 1 µm.

The method may comprise the step of varying the energy of said charged particle beam. This may be so as to allow the electrons in the charged particle beam to penetrate to different depths within the specimen. For example, the time-gated cathodoluminescence maps may be obtained for different charged particle beam energies (or speed). A charged particle beam which has a higher energy will penetrate deeper into the specimen. As the electron penetrates deeper it will excite the specimen at a greater depth, causing cathodoluminescence to be emitted from deeper within the specimen. Therefore the measured cathodoluminescence signal will contain cathodoluminescence which was emitted by deeper regions within the specimen. Accordingly, the measured time-gated cathodoluminescence signal can be deconvolved to provide cathodoluminescence maps from elementary volumes which are buried deeper within the specimen. As a result 3-D cathodoluminescence maps can represent features of the specimen which are located at greater depths within the specimen.

The method may further comprise the step of measuring a time-gated cathodoluminescence map so that each point of the map shows time-gated cathodoluminescence measured for one or more charged particle beam energies. Thus, the amount of depth dependant data may be significantly increased. The use of smaller elementary volumes below the surface is then possible and in turn depth resolution of the deconvoluted cathodoluminescence map can be improved.

The measured time-gated cathodoluminescence may be resolved spectrally. One or more time-gated cathodoluminescence map may then be produced to represent the time-gated cathodoluminescence intensity measured within one or more spectral intervals.

Each of the above-mentioned methods or steps may be applied to a time-gated cathodoluminescence map measured within one spectral interval.

Deconvolved cathodoluminescence maps obtained for different spectral intervals can be combined to form a deconvolved hyperspectral cathodoluminescence map, i.e. a map showing the cathodoluminescence spectrum emitted by each elementary volume for a given set of parameters.

The hyperspectral map may reveal regions of the specimen (i.e. ensembles of one ore more elementary volumes) which emit light within a specific spectral intervals. An ensemble of one or more elementary volumes which emit light within a specific spectral interval is called a spectral region. For example, a first spectral region might emit green luminescence and another red luminescence. Two spectral regions which emit light within different spectral intervals might overlap. For inhomogeneous specimen, e.g. nanostructured specimen, many spectral intervals may coexist.

Once a hyperspectral map has been produced accordingly to the method described here above, it is possible to delay the time-gate so that a delayed time-gated cathodoluminescence signal may be measured which contains cathodoluminescence emitted posteriorly to the cathodoluminescence used in the hyperspectral map. The delayed time-gated cathodoluminescence measurement consists of contributions from: elementary volumes that overlap with the generation volume and; elementary volumes outside of the generation volume to which charge carriers have diffused during the delay time.

If the delayed time-gated cathodoluminescence measurement shows spectral features that are not present within the cathodoluminescence emitted by the generation volume (i.e. within the spectral regions which overlap with the generation volume), it means that electron-hole pairs diffused to one or more spectral regions having the spectral features that the cathodoluminescence emitted by the generation volume misses. For example, the delayed time-gated cathodoluminescence might contain green and blue light while only green light is emitted from the generation volume; charge carriers migrated from the generation volume to spectral regions emitting blue light.

Thus, the delayed time-gated cathodoluminescence is indicative of where charge carriers diffused to during the delay between both time-gates. By varying the delay, it is possible to reconstruct the path followed by charged carriers from one spectral region to the other and to infer their diffusion speed and mobility.

The method would still be valid if the deconvolution step was skipped but the spatial resolution would be limited by the size of the generation volume.

The method may further comprise the steps of: measuring, after a delay period, one or more other time-gated cathodoluminescence; and comparing the one or more other measured time-gated cathodoluminescence to the cathodoluminescence map, to determine if the charged particles have moved within the specimen. The method may comprise the step of comparing the one or more other measured time-gated cathodoluminescence to the cathodoluminescence map, to determine diffusion of the charged particles within the specimen. The one or more time-gated cathodoluminescence measured after a delay period may be used to form a second cathodoluminescence map. The one or more other time-gated cathodoluminescence may have a temporal delay.

According to a further aspect of the present invention there is provided a cathodoluminescence map generating device comprising: a beam generator for generating an intensity modulated charged particle beam; a focusing element for focusing said charged particle beam on a specimen; means for gating temporally the cathodoluminescence emitted by said specimen; means for measuring the time-gated cathodoluminescence for different charged particle beam positions on the specimen and to generate a cathodoluminescence map using the measured time-gated cathodoluminescence; and means for deconvoluting the cathodoluminescence map to improve the resolution of said cathodoluminescence map.

The charged particle beam may be a electron beam or an Ion beam.

The means for deconvoluting the cathodoluminescence map to improve the resolution of said cathodoluminescence map, may comprise means for deconvoluting the cathodoluminescence map to improve the spatial resolution of said cathodoluminescence map. The means for deconvoluting the cathodoluminescence map to improve the resolution of said cathodoluminescence map, may comprise means for deconvoluting the cathodoluminescence map to improve the lateral spatial resolution of said cathodoluminescence map. The means for deconvoluting the cathodoluminescence map to improve the resolution of said cathodoluminescence map, may comprise means for deconvoluting the cathodoluminescence map to improve the depth resolution of said cathodoluminescence map. The means for gating temporally the cathodoluminescence may comprise means for choosing a time-gate such that electron-hole diffusion along a particular direction within the specimen during a time-gate interval is of the same order of magnitude, or smaller than, the improved spatial resolution of said cathodoluminescence map along said direction.

The means for gating temporally the cathodoluminescence may comprise a gate width smaller than about 1 ns. The means for gating temporally the cathodoluminescence may comprise a gate width smaller than 1 ns.

The means for gating temporally the cathodoluminescence may comprise a means to measure directly the time-gated cathodoluminescence so that the cathodoluminescence signal out of the time-gate temporal boundaries is not recorded.

The means for gating temporally the cathodoluminescence may comprise a means to first measure the time-resolved cathodoluminescence and then integrate the measured the time-resolved cathodoluminescence over a time-gate to produce time-gated cathodoluminescence. Thus, the time-resolved cathodoluminescence may also be recorded.

The means for gating temporally the cathodoluminescence may comprise a means to apply an offset to a time gate. Preferably, the offset of the time-gate may be modified. Thus the time gate can be adjusted so that the onset of the time-resolved cathodoluminescence signal is measured.

The cathodoluminescence map generating device may further comprise means for deconvolving cathodoluminescence maps to provide improved lateral resolution and/or depth resolution to said cathodoluminescence maps. Preferably, the cathodoluminescence map generating device further comprises means for deconvoluting the measured time-gated cathodoluminescence to provide a deconvoluted cathodoluminescence map which represents cathodoluminescence emitted from elementary volumes planes which are at different lateral positions or depths of the specimen.

Preferably, the cathodoluminescence map generating device may further comprise means for deconvoluting the measured time-gated cathodoluminescence to provide two or more 2D cathodoluminescence maps each of which represent cathodoluminescence emitted from planes which are at different depths of the specimen.

The beam generator in either of the above-mentioned cathodoluminescence map generating devices may comprise a photocathode.

The beam generator for generating an intensity modulated charged particle beam may be configured to provide a charged particle beam spot which has a diameter smaller than 1 μm.

The cathodoluminescence map generating devices may further comprise means for varying the energy of the charged particle beam. The energy of the charged particle beam may be varied by varying different acceleration voltages applied to said charged particle beam. This may be so as to allow the electrons in the charged particle beam to penetrate to different depths within the specimen.

The cathodoluminescence map generating devices may further comprise means for measuring time-gated cathodoluminescence for different acceleration voltages of said charged particle beam.

The cathodoluminescence map generating devices may further comprise a means to spectrally resolve said time-gated cathodoluminescence.

The cathodoluminescence map generating devices may further comprise: means for varying the acceleration voltage of said charged particle beam, gating temporally the cathodoluminescence emitted by said specimen and means for measuring the time-gated cathodoluminescence; means for measuring time-gated cathodoluminescence for different acceleration voltages of said charged particle beam; means for deconvolving time-gated cathodoluminescence maps and representing three dimensional cathodoluminescence maps.

A device comprising, a laser having a cycle period shorter than about 1 ns; a photocathode; an electron optical lens; an electron deflector; a lens for focusing the laser beam generated by said laser on said photocathode, said photocathode being arranged for generating pulses in response to said laser beam and for delivering electron pulses to a specimen through said electron optical lens and said deflectors for focusing and positing said electron and to excite said specimen, so as to produce cathodoluminescence; a gated light detector having a gate shorter than about 1 ns for gating said cathodoluminescence at different excitation points, so as to produce a time-gated cathodoluminescence map.

The device may further comprise means for deconvolving said time-gated cathodoluminescence map, to improve the resolution of the time-gated cathodoluminescence map.

The device may further comprise means for deconvolving said time-gated cathodoluminescence map so as to produce spatial resolution enhanced cathodoluminescence 2D or 3D maps.

The device may further comprise a mean to spectrally resolve said cathodoluminescence.

The device may further comprise means for modifying the modulated charged particle beam current. This may be so as to allow to control the electron-hole pair density generated within the specimen.

The device may further comprise means to offset the time-gate of said mean to measure time-gated cathodoluminescence.

The device may further comprise means to measure, after a delay period, one or more other time-gated cathodoluminescence; and means for comparing the one or more other measured time-gated cathodoluminescence to the cathodoluminescence map, to determine if the charged particles have moved within the specimen.

BRIEF DESCRIPTION OF THE DRAWINGS

Embodiments of the invention will now be described by way of example only. Reference will be made to.

DETAILED DESCRIPTION OF THE DRAWINGS

Figure 1:
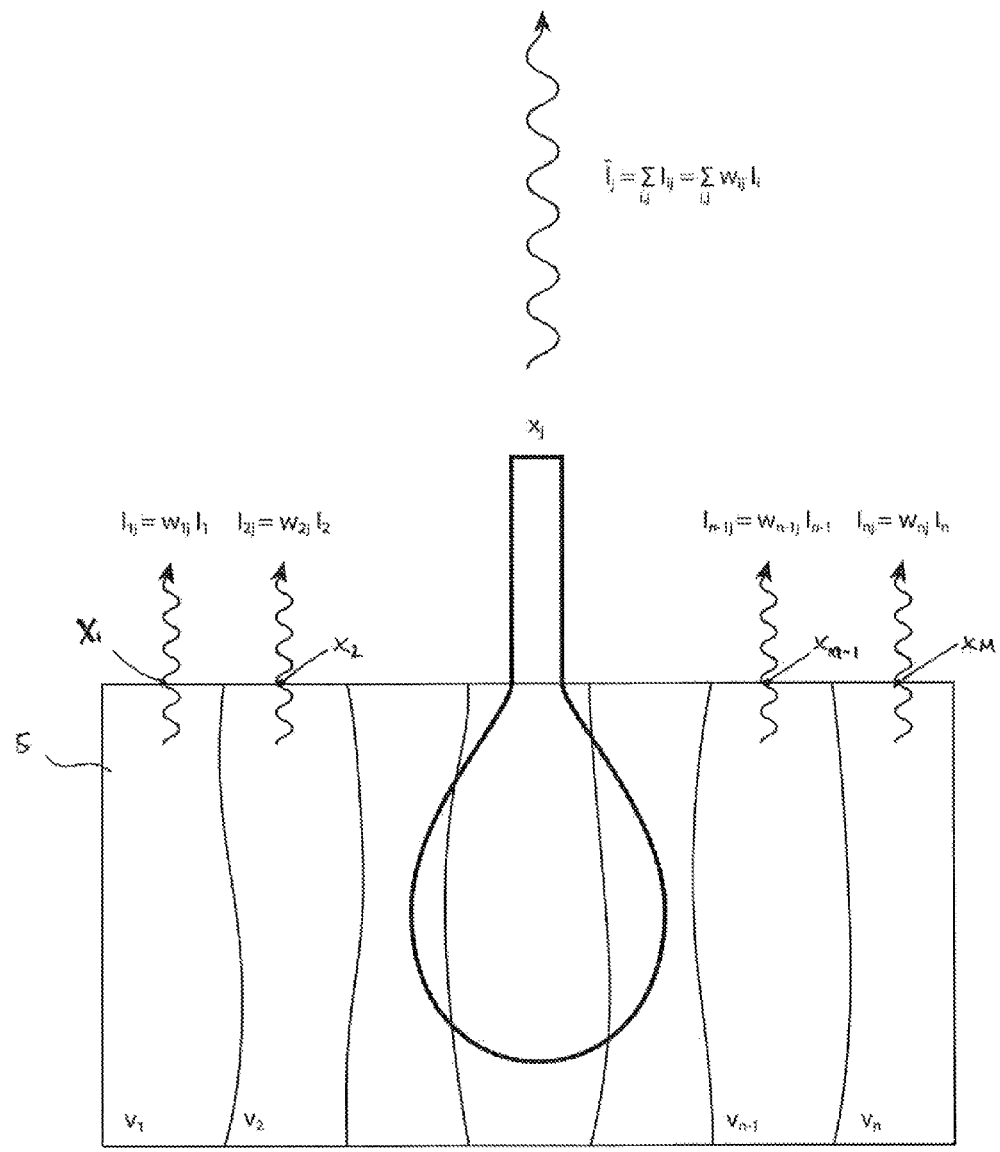
FIG. 1 illustrates the deconvolution step performed in the method of the present invention.

In accordance with the present invention, methods and devices are provided for producing high-resolution cathodoluminescence maps, and in particular for producing cathodoluminescence maps which have improved spatial resolution and/or provide depth resolution e.g. 3D cathodoluminescence maps.

A scanning electron microscope has a photocathode-based electron gun driven by an optical laser. The laser intensity is modulated in such a way that a train of ultrafast photoelectron pulses is generated to form a photoelectron beam. The photoelectron beam is focused on a specimen. The position on a specimen at which the photoelectron beam is focused can be varied using electron optical deflectors or by displacing the specimen.

Electrons within the photoelectron beam excite the specimen upon impact, causing a volume of the specimen to emit a cathodoluminescence signal. The cathodoluminescence signal generated by the interaction of the electron beam with the specimen is measured with an optical measurement device, e.g. a parabolic mirror, and resolved temporally by a measurement device, such as a fast photodiode, a streak camera or any kind of apparatus having a fast response time. The optical measurement device is synchronized to the train of electron pulses so that time-resolved measurements start each time an electron pulse hits the specimen and ends when the next electron pulse hits the specimen. The measurement dynamic and signal over noise ratio can be improved by repeating the time-resolved measurement over many electron pulse excitations. Scanning the electron beam over the specimen and measuring the emitted cathodoluminescence signal as a function of time, produces a time-resolved cathodoluminescence map.

Electrons within the photoelectron beam diffuse within the specimen upon impact, thus causing undesired regions of the specimen to emit a cathodoluminescence signal and contribute to the measured cathodoluminescence signal. The cathodoluminescence signal emitted by these undesired regions of the specimen results in blurring of the time-integrated cathodoluminescence map.

Substantially blur-free cathodoluminescence maps (i.e. cathodoluminescence maps where the effects of diffusion have been accounted for) are obtained by integrating temporally the time-resolved cathodoluminescence map over a time gate delimited by the moment the pulse hits the sample and a given cutoff time. The cutoff time is chosen to be smaller than the carrier lifetime, so that the spatial resolution of the gated cathodoluminescence map is improved over a standard cathodoluminescence map. By choosing the cutoff time to be smaller than the carrier lifetime, the cathodoluminescence in the cathodoluminescence map which resulted from diffusion is reduced from the time-resolved cathodoluminescence map.

The strong reduction of diffusion artifacts obtained on gated cathodoluminescence maps opens a whole new avenue to 2D or 3D spectroscopy of a specimen with nanometer resolution. The resolution of gated cathodoluminescence maps is primarily limited by the size of the generation volume. The accurate shape of the generation volume can be computed, and it is possible to deconvolve a gated cathodoluminescence map. 2D or 3D cathodoluminescence maps can be produced with probe-size limited resolution.

According to a further aspect of the present invention the gated cathodoluminescence maps are deconvoluted to provide 2-D cathodoluminescence maps with improved lateral spatial resolution and/or to provide cathodoluminescence maps with depth resolution (e.g. 3D cathodoluminescence maps).

Firstly, a mesh of the specimen volume is generated which consists of "N" elementary volumes. The cathodoluminescence emitted by each elementary volume will be calculated for a given excitation level, i.e. for a given set of properties (or parameters) of the electron-hole pair gas within the elementary volume. For instance, the cathodoluminescence emitted by each elementary volume might be calculated for the average electron-hole pair density generated during the acquisition of the gated 2-D cathodoluminescence map and a given temperature. As already mentioned, the cathodoluminescence emitted by an elementary volume for a given excitation level is called elementary cathodoluminescence.

Next a modulated electron beam is focused on a surface of the specimen. A generation volume forms below the surface in which electron-hole pairs are generated. The generation volume may overlap with one or more elementary volumes, i.e. electron-hole pairs may be generated in one or more elementary volumes, and, in turn, one or more elementary volumes may contribute to the cathodoluminescence when electron-hole pairs recombine. The cathodoluminescence which is measured is therefore the sum of the contribution of one or more elementary volumes.

By focusing the modulated electron beam to a different point on the surface of the specimen, the position and eventually the form of the generation volume changes so that the number of electron-hole pairs generated in each elementary volumes changes and the contribution of each elementary volumes to the overall cathodoluminescence changes.

Figure 2:
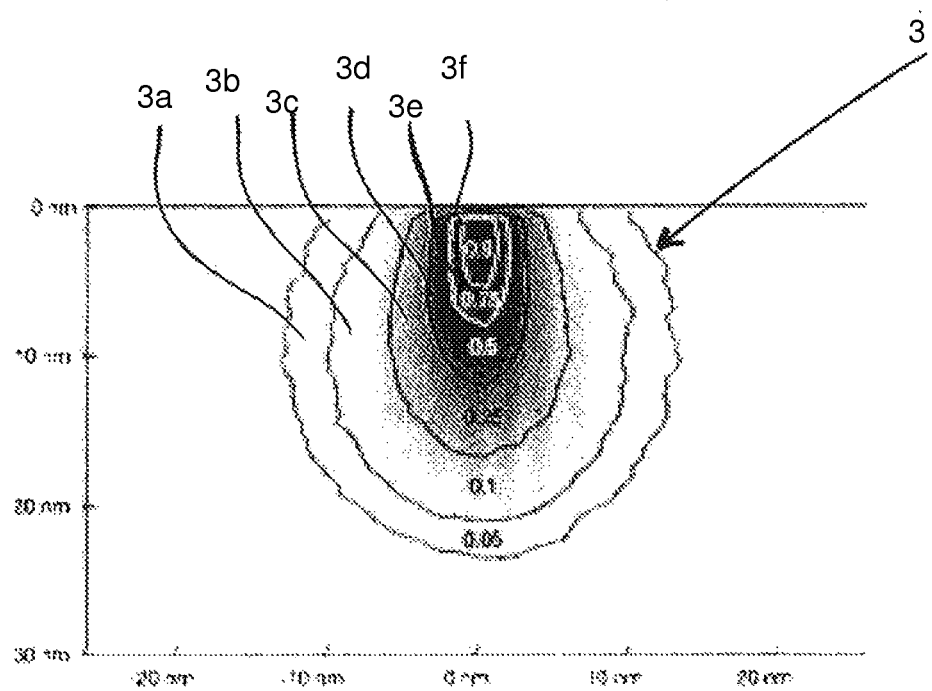
FIG. 2 shows the result of a Monte Carlo simulation for a bulk Gallium Nitride specimen when a 1 keV charged particle beam is focused on the surface of the specimen.

FIG. 2 illustrates the deconvolution step performed in the method of the present invention. FIG. 2 shows a specimen 5 which has been discretized into elementary volumes ($V_1$-$V_n$). Each of the elementary volumes ($V_1$-$V_n$) emit cathodoluminescence ($I_{1j}$-$I_{nj}$) when a excitation beam, such as modulated charged particle beam, is focused at each of a plurality of excitation points $x_1$-$x_m$. The cathodoluminescence ($\tilde{I}_j$) emitted by the specimen is equal to the sum of the cathodoluminescence emitted by each of the elementary volumes ($V_1$-$V_n$) i.e.

$$\tilde{I}_j = \sum_{i,j} I_j \left( \sum_{=i,j} w_{ij} I_j \right).$$

To make subsequent deconvolution possible, the contribution of a elementary volume ($V_1$-$V_n$) in the specimen to the cathodoluminescence ($I_j$) for a given excitation point $x_j$, is expressed as a function of the elementary cathodoluminescence emission for this element, i.e. the cathodoluminescence that would be emitted by an electron-hole pair gas with a given arbitrary set of properties (e.g. the cathodoluminescence that would be emitted for a given arbitrary electron-hole pair density within the elementary volume). The simplest relationship between the elementary cathodoluminescence and the actual mesh cathodoluminescence is a linear expression where the mesh cathodoluminescence is equal to the elementary cathodoluminescence multiplied by a weight e.g. for elementary volume $V_1$, the mesh cathodoluminescence ($I_{1j}$) is equal given by $I_{1j}=w_{1j}I_1$, wherein "w" is the weight given to the elementary cathodoluminescence. The weight may depend on the wavelength. Other, more complicated relationship might also be chosen.

The weight (w) is determined by the properties of the electron-hole pairs that are generated within the elementary volume, i.e. the density of the electron-hole gas within the elementary volume, its distribution, its temperature or any other physical parameter. In the simplest cases, the weight is proportional to the electron-hole pair density within the elementary volume.

The weight (w) may be determined using well-known methods. For example, if the specimen is of a known type, then it is possible to determine the generation volume and the contribution made by different regions within a generation volume to a cathodoluminescence signal emitted by that specimen, based on properties of the specimen. For instance, a known Monte-Carlo simulation method may be used to calculate the electron-hole pair density and a known luminescence model may used to determine the cathodoluminescence intensity as a function of the electron-hole pair density. Alternatively it is possible to determine the generation volume and the contribution made by different regions within a generation volume to a cathodoluminescence signal emitted by that specimen, by carrying out well-known tests on a test sample which is similar to the specimen.

For each of the "m" points on the surface, the emitted cathodoluminescence signal is gated temporally to provide a time-gated cathodoluminescence. The time-gated cathodoluminescence is measured for different electron beam positions on the specimen i.e. each of the "m" points on the surface, to generate a time-gated cathodoluminescence map.

Finally, the time-gated cathodoluminescence map can be deconvoluted. For each of the "m" points on the surface, the weight of each elementary volume is calculated. "m" gated cathodoluminescence measurements give a set of "m" equations relating the elementary cathodoluminescence to the measured cathodoluminescence, which can be solved by a least square method to extract the "n" elementary volumes.

The lateral spatial resolution of each point in the deconvoluted cathodoluminescence map (each point on cathodoluminescence map corresponds to a point on the surface of the specimen at which the electron beam was focused and a cathodoluminescence signal was measured) is now improved, because the contribution made to the measured cathodoluminescence signal by the regions within a generation volume which are lateral to the point on the surface of the specimen at which the intensity modulated electron beam was focused were removed. This was done for each of the points on the time-gated cathodoluminescence map corresponding to each of the different electron beam positions on the specimen, to provide a complete deconvoluted cathodoluminescence map with improved lateral spatial resolution.

Optimal results are obtained when successive generation volumes within the specimen, which result from intensity modulated electron beam being focused on successive points on the surface of the specimen, overlap.

To reduce risks of bad weight calculation, it is possible to measure the time-gated cathodoluminescence maps at different modulated electron beam current, i.e. at different electron-hole pair densities. Usually, measurements obtained at low excitation levels are less sensitive to saturation effects and many-body interactions between electron-hole pairs; the calculation of the weight is much simpler. If by reducing the beam current the result is similar, the weights have been calculated correctly.

FIG. 1 shows the result of a Monte Carlo simulation for a bulk Gallium Nitride specimen when a 1 keV electron beam is focused on the surface of the specimen. The figure shows a generation volume 3, which has been divided into different regions 3a-f each of which contains various concentration of electron-hole pairs as generated by the electron beam. The concentration of electron-hole pairs within each of the regions 3a-f is also indicated by the numbers shown within each of the regions 3a-f; for example, 90% of the electron-hole pairs generated by the electron beam is generated in region 3a.

It is also possible to generate a mesh of the specimen volume consisting of elementary volumes with and without contact to the surface (non-buried i.e. elementary volumes on the surface of the specimen, and buried elementary volumes i.e. elementary volumes which are below the surface of the specimen). In this case, it is possible to deconvolve measured time-gated cathodoluminescence map so that the elementary cathodoluminescence can then be calculated for buried elementary volume as well and provide depth information. The finer the number of buried elements, the finer the depth resolution.

Preferably, this is done by generating a mesh that consists of two or more layers of elementary volumes, so that deconvoluting the measured time-gated cathodoluminescence provides two or more reference cathodoluminescence maps each of which represent cathodoluminescence emitted from planes within the specimen which are at different depths in the specimen. Each of the two or more 2D cathodoluminescence maps provide a 3D cathodoluminescence map.

The depth resolution of the 3D cathodoluminescence maps may be further improved by varying the energy of the electrons in the modulated electron beam which is focused on the surface of the specimen. This can be done, for example, by varying the accelerating voltage applied to electrons in the electron beam or by varying the speed of the electron beam. This will allow the electrons in the electron beam penetrate to different depths within the specimen. Thus more in-depth data is acquired and the deconvolution step can be performed with more and thinner layers of elementary volumes. Also at higher modulated electron beam energy, deeper regions of the specimen will contribute to the measured cathodoluminescence signal so that the 3D cathodoluminescence map may provide spectral information about deeper regions within the specimen.

Firstly, a mesh of the specimen volume is generated which consists of 'n' elementary volumes, one or more of the 'n' elementary volumes being buried. The cathodoluminescence emitted by each elementary volume will be calculated for a given excitation level, i.e. for a given set of properties of the electron-hole pair gas within the elementary volume. For instance, the cathodoluminescence emitted by each elementary volume might be calculated for the average electron-hole pair density generated during the acquisition of the gated 2-D cathodoluminescence map.

Next a modulated electron beam with a specified beam energy is focused on a surface of the specimen. A generation volume forms below the surface in which electron-hole pairs are generated. The generation volume may overlap with one or more elementary volumes, i.e. electron-hole pairs may be generated in one or more elementary volumes, and, in turn, one or more elementary volumes may contribute to the cathodoluminescence when electron-hole pairs recombine. The cathodoluminescence which is measured is therefore the sum of the contribution of one or more elementary volumes, one more of those elements being buried.

By changing the focus point of the modulated electron beam to a different point on the surface of the specimen and/or by varying the modulated electron beam energy, the position and eventually the form and the overall volume of the generation volume changes so that the number of electron-hole pairs generated in each elementary volumes changes and the contribution of each elementary volumes to the overall cathodoluminescence changes.

To make subsequent deconvolution possible, the contribution of a elementary volume to the cathodoluminescence for a given excitation point, is expressed as a function of the elementary cathodoluminescence emission for this element, i.e. the cathodoluminescence that would be emitted by an electron-hole pair gas with a given arbitrary set of properties (e.g. the cathodoluminescence that would be emitted for a given arbitrary electron-hole pair density within the elementary volume). The simplest relationship between the elementary cathodoluminescence and the actual mesh cathodoluminescence is a linear expression where the mesh cathodoluminescence is equal to the elementary cathodoluminescence multiplied by a weight. The weight may depend on the wavelength.

The weight is determined by the properties of the electron-hole pairs that are generated within the elementary volume, i.e. the density of the electron-hole gas within the elementary volume, its distribution, its temperature or any other physical parameter. In the simplest cases, the weight is proportional to the electron-hole pair density within the mesh cell.

The weight may be determined using well-known methods. For example, if the specimen is of a known type, then it is possible to determine the generation volume and the contribution made by different regions within a generation volume to a cathodoluminescence signal emitted by that specimen, based on properties of the specimen. For instance, a known Monte-Carlo simulation method may be used to calculate the electron-hole pair density and a known luminescence model may used to determine the cathodoluminescence intensity as a function of the electron-hole pair density. Alternatively it is possible to determine the generation volume and the contribution made by different regions within a generation volume to a cathodoluminescence signal emitted by that specimen, by carrying out well-known tests on a test sample which is similar to the specimen.

For each of the set of "m" measurements where the excitation point on the surface or the beam energy has been modified, the emitted cathodoluminescence signal is gated temporally to provide a time-gated cathodoluminescence. The time-gated cathodoluminescence is measured for different electron beam positions and beam energies on the specimen to generate a set of gated cathodoluminescence measurements.

Finally, the set of gated cathodoluminescence measurements can be deconvoluted. For each of the "m" measurements, the weight of each elementary volume is calculated. "m" gated cathodoluminescence measurements give a set of "m" equations, relating the elementary cathodoluminescence to the measured cathodoluminescence, which can be solved by a least square method to extract the cathodoluminescence signal coming from each region within each of the "n" generation volumes.

The lateral spatial resolution of each point in said cathodoluminescence map (each point on cathodoluminescence map corresponds to a point on the surface of the specimen at which the electron beam was focused and a cathodoluminescence signal was measured) is now improved, because the contribution made to the measured cathodoluminescence signal by the regions within a generation volume which are lateral to the point on the surface of the specimen at which the intensity modulated electron beam was focused were removed. Furthermore, depth resolution has been gained because the contribution coming from elementary volumes at different depth could be extracted.

In a typical embodiment, an ultrafast laser is used, which generates 100 fs laser pulses at a repetition rate of 80 MHz. The laser beam is focused on a photocathode, which then generates a beam of subpicosecond photoelectron pulses that are focused on a semiconductor specimen of bulk GaAs. The diffusion length in GaAs is approximately 2-4 µm with a mobility of about 4 nm/ps at 4K. By choosing a cut-off time of 1 ps, the diffusion is about 4 nm, i.e. three orders of magnitude smaller than in the case no gating had been used. A mesh made of 100×100×100 cubic cells of 10 nm width is chosen. 100×100 gated cathodoluminescence measurements are performed by exciting the centre of each grid element at the surface. The measurement is repeated for a set of 100 acceleration voltages. For each excitation point and acceleration voltage, the electron density in each cubic cell (elementary volume) is calculated and the weight relating the cathodoluminescence emitted by each one of the cubic cell to their elementary cathodoluminescence is calculated according to a known theoretical model. A set of 100×100×100 equation is written which is solved with a least square method. A 3D cathodoluminescence map having a resolution of 10 nm is obtain after deconvolving all equations.

The duration of the laser pulses is preferably in a range between 10 fs and 3 ns, preferably between 50 fs and 100 fs. The repetition rate is preferably between 1 KHz and 1 GHz. The grid is not necessary cubic, but preferably comprises any number of cells between 2×2×2 and 1000×1000×1000 cells. The size of the cells is preferably comprised between 0.1 nm and 1 μm, preferably between 1 nm and 100 nm. The number of accelerations voltages is preferably between 1 and 1000.

In an embodiment, the diffusion length in the specimen is negligible. In this case, the time-gated step is skipped. Only deconvolution is performed. Rather than skipping time-gate step, an arbitrarily long time-gate can also be used.

In an embodiment, an offset is added to the time-gate so that a different part of the time-resolved cathodoluminescence is measured. The gate itself can be square-shaped but can also be Gaussian, Lorentzian or have an arbitrary shape.

In an embodiment, any selection of one or more of the following features is included:

The electron gun comprises a photocathode.
The time-gate has a width shorter than 1ns.
The beam spot is smaller than 1 μm.
The energy of the electron beam can be modified.
The gated-cathodoluminescence is deconvolved into a 2D space resolution enhanced cathodoluminescence map.
The gated cathodoluminescence is deconvolved into a 3D space resolution enhanced cathodoluminescence map.
The energy of the electron beam is varied.
The cathodoluminescence is resolved spectrally.
The deconvolution is done by choosing a mesh and working out the contribution of each elementary volume element to the measured cathodoluminescence.

A Monte Carlo simulation is performed to calculate the weight (contribution) of each elementary volume element to the measured cathodoluminescence.

A method is applied to calculate the weight of each elementary volume element to the measured cathodoluminescence.

The deconvolution is done by solving a system of multiple equations. If it is over determined, a fitting method is used, such as a least square method.

The deconvolution is done for each measured spectral intervals.

Various modifications and variations to the described embodiments of the invention will be apparent to those skilled in the art without departing from the scope of the invention as defined in the appended claims. Although the invention has been described in connection with specific preferred embodiments, it should be understood that the invention as claimed should not be unduly limited to such specific embodiment.

The invention claimed is:

1. A method for generating a cathodoluminescence map comprising the steps of:
generating an intensity modulated charged particle beam;
focusing said charged particle beam on a specimen;
gating temporally the cathodoluminescence emitted by said specimen to provide time-gated cathodoluminescence;
measuring the time-gated cathodoluminescence for different charged particle beam positions on the specimen to generate a cathodoluminescence map;
deconvoluting the cathodoluminescence map to improve the resolution of said cathodoluminescence map.

2. A method according to claim 1 wherein the step of deconvoluting the cathodoluminescence map comprises the steps of, discretizing at least part of a volume of the specimen into a region of elementary volumes; and determining the cathodoluminescence emitted by different elementary volumes within the specimen.

3. The method according to claim 1 wherein the step of deconvoluting the cathodoluminescence map further comprises the step of defining a set of parameters which describe an excitation state of the elementary volumes.

4. A method according to claim 1 wherein the step of deconvoluting the cathodoluminescence map further comprises the step of, removing from the cathodoluminescence map the contribution of cathodoluminescence made by elementary volumes of the specimen which are located lateral of a position on the specimen which the electron beam was focused.

5. A method according to claim 1 wherein the step of deconvoluting the measured time-gated cathodoluminescence to improve the resolution to said cathodoluminescence map, comprises the step of deconvoluting the measured time-gated cathodoluminescence to improve the spatial lateral resolution and/or depth resolution of said cathodoluminescence map.

6. A method according to claim 1 further comprising the step of, deconvoluting the measured time-gated cathodoluminescence to provide two or more 2D cathodoluminescence maps each of which represents cathodoluminescence emitted from planes which are at different depths of the specimen.

7. A method according to claim 1 further comprising the step of, varying the energy of said charged particle beam so that particles within the charged particle beam are made to penetrate the specimen to varying depths.

8. A method according to claim 7 further comprising the step of, measuring time-gated cathodoluminescence for different energies of said charged particle beam.

9. A method according to claim 1 further comprising the step of, resolving cathodoluminescence maps spectrally.

10. The method according to claim 1 further comprising the steps of: measuring, after a delay period, one or more other time-gated cathodoluminescence; and comparing, the one or more other measured time-gated cathodoluminescence to the cathodoluminescence map, to determine if the charged particles have moved within the specimen.

11. A cathodoluminescence map generating device comprising: a beam generator for generating an intensity modulated charged particle beam; a focusing element for focusing said charged particle beam on a specimen;
means for gating temporally the cathodoluminescence emitted by said specimen;
means for measuring the time-gated cathodoluminescence for different electron beam positions on the specimen; and
means for forming a cathodoluminescence map using the measured time-gated cathodoluminescence; and
means for deconvoluting the time cathodoluminescence map to improve the resolution of said cathodoluminescence map.

12. A cathodoluminescence map generating device according to claim 11 wherein the means for deconvoluting the cathodoluminescence map to improve the resolution of said cathodoluminescence map, is a means configured to deconvolute the cathodoluminescence map to improve the lateral spatial resolution and/or depth resolution of said cathodoluminescence map.

13. A cathodoluminescence map generating device according to claim 11 further comprising, means for deconvoluting the measured time-gated cathodoluminescence to provide two or more 2D cathodoluminescence maps each of which represent cathodoluminescence emitted from planes which are at different depths of the specimen.

14. A cathodoluminescence map generating device according to claim 11 wherein, the beam generator comprises a photocathode.

* * * * *

UNITED STATES PATENT AND TRADEMARK OFFICE
CERTIFICATE OF CORRECTION

| | |
|---|---|
| PATENT NO. | : 8,674,320 B2 |
| APPLICATION NO. | : 13/795291 |
| DATED | : March 18, 2014 |
| INVENTOR(S) | : Jean Berney |

Page 1 of 1

It is certified that error appears in the above-identified patent and that said Letters Patent is hereby corrected as shown below:

In the specification, column 17, line 21 please replace - ins - with "1 ns"

Signed and Sealed this
First Day of July, 2014

Michelle K. Lee
*Deputy Director of the United States Patent and Trademark Office*